United States Patent [19]

Mondet et al.

[11] Patent Number: 5,116,601
[45] Date of Patent: May 26, 1992

[54] AEROSOL HAIR SPRAY CONTAINING A TETRAPOLYMER OF ACRYLIC ACID, N,N-DIMETHYLACRYLAMIDE, N-TERT-BUTYLACRYLAMIDE, AND ETHYL METHACRYLATE AND A NON-HALOGENATED PROPELLANT GAS

[75] Inventors: Jean Mondet, Drancy; Christos Papantoniou, Montmorency; Jean-Charles Cheneble, Bondy; Claude Mahieu, Paris, all of France

[73] Assignee: L'Oreal, Paris, France

[21] Appl. No.: 655,348

[22] Filed: Feb. 14, 1991

[30] Foreign Application Priority Data

Feb. 16, 1990 [FR] France ............... 90 01917

[51] Int. Cl.⁵ ............................... A61K 7/06
[52] U.S. Cl. ............................ 424/47; 424/43; 424/45; 424/70; 424/71; 424/DIG. 1; 424/DIG. 2
[58] Field of Search ............ 424/47, 43, 70, 71, 424/81, DIG. 1, DIG. 2, 45

[56] References Cited

U.S. PATENT DOCUMENTS 3,692,893  9/1972  Palmer ................... 424/47
3,927,199  12/1975 Micchelli et al. ....... 424/47
4,192,861  3/1980  Micchelli et al. ....... 424/47
4,859,455  8/1989  Nowak, Jr. et al. ..... 424/47
5,019,377  5/1991  Torgerson ............... 424/70

FOREIGN PATENT DOCUMENTS 1192135  8/1985  Canada.
3518847  12/1985  Fed. Rep. of Germany.

Primary Examiner—Thurman K. Page
Assistant Examiner—Robert H. Harrison
Attorney, Agent, or Firm—Oliff & Berridge

[57] ABSTRACT

A cosmetic composition in the form of an aerosol spray for hair control contains a solvent; a film-forming tetrapolymer resulting from the copolymerization of (a) 5 to 10 wt. % acrylic acid, (b) 20 to 52 wt. % N,N-dimethylacrylamide, (c) 3 to 28 wt. % of N-tert-butylacrylamide, and (d) 20 to 45 wt. % ethyl methacrylate, the carboxylic acid functions of the tetrapolymer being at least partially neutralized with a mineral or organic base; and at least one non-halogen propellant gas. This spray provides excellent hair control, and the film-forming substance does not cause stickiness of the hair over time and is easily eliminated by washing with a shampoo.

14 Claims, No Drawings

AEROSOL HAIR SPRAY CONTAINING A TETRAPOLYMER OF ACRYLIC ACID, N,N-DIMETHYLACRYLAMIDE, N-TERT-BUTYLACRYLAMIDE, AND ETHYL METHACRYLATE AND A NON-HALOGENATED PROPELLANT GAS

The present invention is a cosmetic composition in the form of an aerosol spray for controlling hair, containing as the film-forming agent a tetrapolymer of acrylic acid, N,N-dimethylacrylamide, N-tert-butylacrylamide, and ethyl methacrylate, the propellant gas being of the non-halogenated type.

BACKGROUND

For ecological reasons, the current trend in hair spray cans is systematically to replace halogenated propellant gases of the Freon type by hydrocarbons, in particular by propane, butane, or mixtures thereof. However, this substitution cannot be made without profoundly changing the formulations both as concerns the ratios between the ingredients and as concerns the actual nature of the ingredients, particularly the film-forming substances. It is well known that an aerosol hair spray must meet certain criteria. Among these, the hair control properties in a highly moist atmosphere without the hair being observed to become sticky should be mentioned in particular.

Between two shampooings, the hair should retain good cosmetic properties to the touch, should not become sticky or greasy, and the hairs should untangle easily without clinging to each other, particularly when the shampooings are at least a week apart.

It is also important for the film-forming substance to be easily eliminated when the hair is washed. Finally, after application of the aerosol spray, the hair should look natural and it should be possible to comb it without formation of powder.

All these properties have been demonstrated for certain polymers which have been used for making aerosol sprays whose propellant was essentially a mixture of halogenated hydrocarbons, in particular mixtures of monofluorotrichloromethane and dichlorodifluoromethane.

Polymers such as those based on vinyl acetate and crotonic acid have, however, proved to be unusable in the presence of non-halogenated propellant gases.

Hence, recent work has focused on the choice of new polymers that might not only be compatible with non-halogenated propellant gases but also have excellent cosmetic properties.

In this connection, one may cite European Patent Number 0,062,002, which describes a hair control composition containing, as the film-forming substance, a terpolymer resulting from copolymerization of:

a) 40 to 60 wt.% of an N-alkylacrylamide or an N-alkyl methacrylamide with 1 to 4 carbon atoms in the alkyl part, with b) 35 to 50 wt.% of a $C_1$-$C_4$ alkyl ester or a $C_1$-$C_4$ hydroxyalkyl ester of acrylic acid or methacrylic acid, and c) 3 to 11 wt.% of acrylic acid or methacrylic acid relative to the total monomer mixture and a proportion of at least 50% of carboxyl groups present in the terpolymer being neutralized by a lower organic base chosen from 2-amino-2-methyl-propanol, 2-amino-2-methyl-1,3-propanediol, triethanolamine, and triisopropanolamine, the propellant gas being a non-halogenated hydrocarbon such as propane or butane or a mixture thereof.

Although the choice of monomers of this terpolymer gave good compatibility with non-halogenated hydrocarbons, it was, however, found that some of the cosmetic properties of the aerosol sprays were not totally satisfactory.

In particular, the spray was observed to be insoluble when shampooed and sometimes the hair became very sticky about seven days after the application of the spray.

SUMMARY OF THE INVENTION

After several studies on a very large number of copolymers, it has now been found, quite surprisingly and unexpectedly, that excellent cosmetic properties as well as very good compatibility with non-halogenated propellant gases could be obtained by using a tetrapolymer containing units of acrylic acid, N,N-dimethylacrylamide, N-tertbutylacrylamide, and ethyl methacrylate.

These studies have shown not only the importance of the choice of monomer but also the crucial nature of the proportion of each monomer.

Hence, the present invention is directed to a cosmetic composition in the form of an aerosol spray for controlling hair, containing in a solvent, as a film-forming substance, a tetrapolymer resulting from copolymerization of:

(a) 5 to 10 wt.% acrylic acid (AA), preferably 5 to 8 wt.%;
(b) 20 to 52 wt.% N,N-dimethylacrylamide (DMA), preferably 25 to 45 wt.%;
(c) 3 to 28 wt.% N-tert-butylacrylamide (NtBA), preferably 5 to 25 wt.%; and
(d) 20 to 45 wt.% ethyl methacrylate (EMA), preferably 25 to 40 wt.%;

the carboxylic acid functions of said tetrapolymer being partially or totally neutralized with a mineral or organic base; and at least one non-halogenated compound as a propellant gas.

The good properties of aerosol sprays according to the invention are due essentially to the choice of monomers of the tetrapolymer and their respective proportions, which vary only in a relatively narrow and critical range.

The rate of neutralization of the carboxylic functions of the tetrapolymer is at least 50% and preferably between 70 and 100%.

Of the mineral bases that may be used, the following may be cited in particular: sodium hydroxide, potassium hydroxide, ammonia; organic bases such as primary, secondary, or tertiary amines; alkanolamines such as triethanolamine or triisopropanolamine; hydroxyamines such as 2-amino-2-methyl-propanol (AMP) and 2-amino-2-methyl-1,3-propanediol (AMPD).

The tetrapolymer of the aerosol sprays according to the invention should preferably have a molecular weight such that its absolute viscosity is between 2 and 5 cP (measured in solution in 5% DMF at 34.6° C.) and preferably between 2.3 and 4.5 cP.

In aerosol sprays according to the invention, the tetrapolymer is generally present in solution in an organic solvent at a concentration of between 0.5 and 5 wt.%, preferably between 1 and 4 wt.%, relative to the total weight of the composition. The solvent is preferably a lower alcohol present in a concentration of between 40 and 60 wt.%; ethanol, isopropanol, and mixtures thereof being preferred. The proportion of non-halogenated propellant gas is generally between 40 and 65 wt.% and preferably between 45 and 60%.

The propellant gas preferably used for aerosol sprays according to the invention is a non-halogenated hydrocarbon such as propane, n-butane, isobutane, or mixtures thereof. Preferred propellant gases include propane-butane mixtures in a ratio of 1:10 to 1:2, or dimethyl ether or a mixture of these propellant gases.

Of course, aerosol sprays according to the invention can also contain other ingredients conventional for this type of composition such as plasticizers, softeners, perfumes, oils, lubricants, lanolin, silicones, sunscreens, and dyes.

According to the invention, it is desirable for the vapor pressure in the aerosol can to be between about 2.5 and 5 bars at 25° C.

The tetrapolymer of the aerosol sprays according to the invention can be obtained by conventional polymerization techniques, including bulk, solution, suspension, dispersion, or emulsion polymerization, without the essential characteristics of the tetrapolymer obtained being affected thereby.

The polymerization reaction may be initiated with the aid of any conventional catalyst such as azobisisobutyronitrile or organic peroxide compounds such as lauroyl peroxide or benzoyl peroxide.

In order to adjust the molecular weight, it may be desirable to use chain transfer agents such as thiols, for example, mercaptoethanol or dodecanethiol or accelerators which increase the reaction rate.

According to one preferred embodiment, polymerization is conducted in solution, preferably in ethanol, and at the end of polymerization, the tetrapolymer is isolated by precipitation, preferably in petroleum ether. According to this embodiment, solution polymerization is generally conducted at a temperature between 40° and 90° C. and preferably between 45° C. and 80° C.

Several examples of preparing tetrapolymers and several examples of aerosol sprays containing them will now be provided as an illustration without being limiting in nature.

EXAMPLE 1:

Preparation of the "Acrylic Acid (AA) N,N-dimethylacrylamide (DMA) 40%/N-tert-butylacrylamide (NtBA) 19%/Ethyl Methacrylate (EMA) 35%" Tetrapolymer 12 g of acrylic acid, 80 g of N,N-dimethylacrylamide, 38 g of N-tert-butylacrylamide, and 70 g of ethyl methacrylate are placed in a flask, with agitation and under nitrogen.

200 g of ethanol and 2 g of azobisisobutyronitrile are then added as a catalyst.

The mixture is then heated with agitation for 30 minutes at 74° C., then held at this temperature for about 8 hours.

After cooling, it is diluted with 600 g of ethyl acetate and the tetrapolymer obtained is precipitated in 1 of petroleum ether.

After purification and drying under vacuum, the expected tetrapolymer is obtained with a yield of 98%.

Viscosity ($\eta$): 3.40 cP (measured in a 5% solution in DMF at 34.6° C.)
  Acid index (AI): 47
  Glass transition temperature (Tg): 108 (measured in DSC in a Perkin-Elmer DSC 4 calibrated to the melting point of indium, at a heating rate of 20° C./min).

The tetrapolymers tabulated in Table I below were also prepared by the same method:

TABLE I

| Examples | AA % | DMA % | NtBA % | EMA % | Yield | $\eta$ | IA | Tg °C. |
|---|---|---|---|---|---|---|---|---|
| 2 | 10 | 36 | 19 | 35 | 98 | 3.20 | 76 | 117 |
| 3 | 9 | 47 | 19 | 25 | 98 | 3.26 | 68 | 124 |
| 4 | 6 | 37 | 13 | 44 | 98 | 3.02 | 43 | 103 |
| 5 | 8 | 32 | 25 | 35 | 99 | 3.04 | 57 | 112 |
| 6 | 7 | 29 | 19 | 45 | 99 | 2.92 | 55 | 105 |
| 7 | 5 | 47 | 13 | 35 | 100 | 2.84 | 35 | 108 |
| 8 | 8 | 45 | 5 | 42 | 100 | 3.10 | 61 | 101 |
| 9 | 8 | 40 | 10 | 42 | 99 | 3.03 | 61 | 102 |
| 10 | 8 | 30 | 20 | 42 | 100 | 3.00 | 61.6 | 104 |
| 11 | 6 | 43 | 25 | 26 | 100 | 3.14 | 44 | 122 |
| 12 | 5 | 51 | 19 | 25 | 94 | 3.12 | 37 | 117 |
| 13 | 8 | 25 | 25 | 42 | 93 | 3.05 | 63 | 106 |

EXAMPLES OF AEROSOL SPRAYS

Example A

An aerosol hair spray is prepared by packing in an aerosol can 2 g of tetrapolymer prepared according to Example 1, 100% neutralized (according to the acid index) with AMP, and 40 g of anhydrous ethanol. The following are then introduced by conventional techniques: 58 g of a propellant mixture composed of 55 parts butane, 10 parts propane, and 35 parts isobutane, after which the valve is installed and the can is hermetically sealed (pressure: 4 bars).

When the product is sprayed onto natural or sensitized hair, it is seen to have good control, does not make the hair sticky to the touch after several days, the hair untangles easily, and there is only a slight powdering effect.

After several days without shampooing, these properties are retained. The hair does not become greasy or sticky and its condition is excellent.

After shampooing, the film-forming substance is fully eliminated and the hair has good untangling and softness properties and is pleasant to the touch.

Example B

An aerosol hair spray is prepared by packing in an aerosol can: 2 g of the tetrapolymer prepared according to Example 10, 100% neutralized (according to the acid index) with AMP, and 43 g of anhydrous ethanol. Next, 55 g of a propellant mixture composed of 55 parts butane, 10 parts propane, and 35 parts isobutane is introduced, the valve is installed, and the can is hermetically sealed (pressure 4.3 bars).

Example C

An aerosol hair spray is prepared by packing in an aerosol can 2 g of the tetrapolymer prepared according to Example 11, 100% neutralized (according to the acid index) with AMP, and 43 g of anhydrous ethanol. Next, 55 g of a propellant mixture composed of 55 parts butane, 10 parts propane, and 35 parts isobutane is introduced, the valve is installed, and the can is hermetically sealed (pressure 4.5 bars).

For the sprays in Examples B and C above, the same good properties as those obtained for the aerosol spray in Example A were obtained upon application to natural or sensitized hair.

COMPARATIVE EXAMPLE

In order to demonstrate the importance not only of the choice of the tetrapolymer monomers but also their relative proportions in the cosmetic properties of the aerosol sprays according to the invention, the polymers listed in Table II were tested for stickiness and solubility of film-forming substance. These tests were conducted under the following conditions:

1. Stickiness Test 5 g of a 10 wt.% ethanol solution of polymer 100% neutralized by AMP is placed in a 25 cc Teflon-coated mold, then the solvent is evaporated for 24 hours at room temperature and the film is removed from the mold. The stickiness of the two surfaces of the film is estimated by touch, by a panel of five persons.

2. Solubility Test 2 g of a 10 wt.% ethanol solution of polymer, 100% neutralized by AMP, is placed in a 55 mm diameter crystallizing dish, then the solvent is evaporated for 24 hours at room temperature. 20 g of a 1.4% aqueous solution of sodium lauryl sulfate is poured onto the dry film; dissolution must be complete under magnetic agitation in less than 15 minutes, giving a clear solution.

TABLE II

| Monomers | Example Ref 1' | Example 8 | Example 9 | Example 10 | Example 13 | Example Ref 2' | Example Ref 3' |
|---|---|---|---|---|---|---|---|
| AA | 8 | 8 | 8 | 8 | 8 | 8 | 8 |
| DMA | 50 | 45 | 40 | 30 | 25 | 20 | 0 |
| NtBA | 0 | 5 | 10 | 20 | 25 | 30 | 50 |
| EMA | 42 | 42 | 42 | 42 | 42 | 42 | 42 |
| Cosmetic | St | NSt | NSt | NSt | NSt | NSt | NSt |
| Properties* | So | So | So | So | So | NSo | NSo |

*St = sticky NSt = not sticky So = soluble in shampoo NSo = not soluble in shampoo As can be seen from Table II, only the tetrapolymers of Examples 8, 9, 10 and 13, in which the four monomers are present in the proportions by weight indicated above, have cosmetically satisfactory properties.

Under the same conditions as above, the tetrapolymers of Examples 1 to 7, 11, and 12 were tested and also proved not to be sticky and to be soluble in the shampoos.

What is claimed is:

1. Cosmetic composition in the form of an aerosol spray for hair control, comprising, as a film-forming substance, a tetrapolymer resulting from the copolymerization of:
   (a) 5 to 10 wt.% acrylic acid;
   (b) 20 to 52 wt.% N,N-dimethylacrylamide;
   (c) 3 to 28 wt.% N-tert-butylacrylamide; and
   (d) 20 to 45 wt.% ethyl methacrylate;
   the carboxylic acid functions of said tetrapolymer being at least 50% neutralized with a mineral or organic base, a solvent for said tetrapolymer; and, a non-halogenated gas.

2. Cosmetic composition according to claim 1, wherein the tetrapolymer results from copolymerization of:
   (a) 5 to 8 wt.% acrylic acid;
   (b) 25 to 45 wt.% N,N-dimethylacrylamide;
   (c) 5 to 25 wt.% N-tert-butylacrylamide; and
   (d) 25 to 40 wt.% ethyl methacrylate.

3. Cosmetic composition according to claim 1, wherein the absolute viscosity of the tetrapolymer is between 2 and 5 cP measured in solution in 5% DMF at 34.6° C.

4. Cosmetic composition according to claim 1, wherein carboxylic acid functions of the tetrapolymer are between 70 and 100% neutralized.

5. Composition according to claim 1, wherein carboxylic acid functions of the tetrapolymer are neutralized with a mineral base selected from the group consisting of, sodium hydroxide, potassium hydroxide and ammonia.

6. Cosmetic composition according to claim 1, wherein carboxylic acid functions of the tetrapolymer are neutralized with an organic base selected from the group consisting of triethanolamine, triisopropanolamine, 2-amino-2-methyl-propanol, and 2-amino-2-methyl-1,3-propanediol.

7. Cosmetic composition according to claim 1, wherein the tetrapolymer is present in a concentration of between 0.5 and 5% relative to the total weight of the composition.

8. Cosmetic composition according to claim 1, wherein the tetrapolymer is present in a concentration of between 1 and 4 wt.% relative to the total weight of the composition.

9. Cosmetic composition according to claim 1, wherein the propellant gas is present in a proportion of between 40 and 65 wt.%.

10. Cosmetic composition according to claim 1, wherein the non-halogenated propellant gas is a non-halogenated hydrocarbon selected from the group consisting of propane, n-butane, isobutane, and mixtures thereof.

11. Cosmetic composition according to claim 11, wherein the non-halogenated propellant gas is a propane-butane mixture in a ratio of 1:10 to 1:2.

12. Cosmetic composition according to claim 1, wherein the non-halogenated propellant gas is dimethyl ether or a mixture thereof with at least one non-halogenated hydrocarbon.

13. Cosmetic composition according to claim 1, wherein the solvent is present in a proportion of between 40 and 60 wt.% relative to the total weight of the composition.

14. Cosmetic composition according to claim 1, the solvent is ethanol, isopropanol, or a mixture thereof.

* * * * *